(12) United States Patent
Young et al.

(10) Patent No.: US 9,656,057 B2
(45) Date of Patent: May 23, 2017

(54) LEAD AND A SYSTEM FOR MEDICAL APPLICATIONS

(71) Applicant: MEDTRONIC BAKKEN RESEARCH CENTER B.V., Maastricht (NL)

(72) Inventors: Edward Willem Albert Young, Maastricht (NL); Sëbastien Jody Ouchouche, Waalre (NL); Sjaak Deckers, Waalre (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 0 days.

(21) Appl. No.: 14/950,549

(22) Filed: Nov. 24, 2015

(65) Prior Publication Data

US 2016/0144165 A1    May 26, 2016

Related U.S. Application Data

(60) Provisional application No. 62/084,311, filed on Nov. 25, 2014.

(51) Int. Cl.
*A61N 1/00* (2006.01)
*A61N 1/05* (2006.01)
(Continued)

(52) U.S. Cl.
CPC .......... *A61N 1/0534* (2013.01); *A61B 5/0478* (2013.01); *A61B 2562/0209* (2013.01);
(Continued)

(58) Field of Classification Search
CPC ...... A61B 2562/0209; A61B 2562/043; A61B 5/0478; A61N 1/0534; A61N 1/36067; A61N 1/36096; H05K 3/28
See application file for complete search history.

(56) References Cited

U.S. PATENT DOCUMENTS

| 6,024,702 A | 2/2000 | Iversen |
| 6,757,970 B1 | 7/2004 | Kuzma et al. |

(Continued)

FOREIGN PATENT DOCUMENTS

| EP | 2653187 A1 | 10/2013 |
| EP | 2656875 A1 | 10/2013 |

(Continued)

OTHER PUBLICATIONS

U.S. Appl. No. 14/951,304, filed by Decré, Michel Marcel José, on Nov. 24, 2015.

(Continued)

*Primary Examiner* — George Manuel
(74) *Attorney, Agent, or Firm* — Shumaker & Sieffert, P.A.

(57) ABSTRACT

In some examples, the present disclosure relates to an implantable medical lead and medical device systems employing such leads for medical applications, such as, e.g., neural stimulation, deep brain stimulation, and/or sensing of bioelectrical signals. In one example, the lead includes a thin film configured to be secured to at least a portion of a carrier core, wherein the thin film has a distal end, a proximal end, and at least one electrode between the proximal end and the distal end; and at least one fixation element configured to secure the distal end of the thin film to the carrier core, wherein the fixation element comprises at least one of a distal extension portion of the thin film at least partially wrapped around the carrier core distal to the at least one electrode or a jacket tube located around the carrier core and the thin film.

31 Claims, 9 Drawing Sheets

(51) Int. Cl.
  *A61B 5/0478* (2006.01)
  *A61N 1/36* (2006.01)
  *H05K 1/02* (2006.01)

(52) U.S. Cl.
  CPC ..... *A61B 2562/043* (2013.01); *A61N 1/36067* (2013.01); *A61N 1/36096* (2013.01); *H05K 1/028* (2013.01)

(56) References Cited

U.S. PATENT DOCUMENTS

| | | | |
|---|---|---|---|
| 6,939,338 | B2 | 9/2005 | Waldhauser et al. |
| 7,941,202 | B2 | 5/2011 | Hetke et al. |
| 8,494,641 | B2 | 7/2013 | Boling et al. |
| 8,565,894 | B2 | 10/2013 | Vetter et al. |
| 8,788,064 | B2 | 7/2014 | Mercanzini et al. |
| 2008/0140152 | A1 | 6/2008 | Imran et al. |
| 2011/0093052 | A1 | 4/2011 | Anderson et al. |
| 2011/0224765 | A1 | 9/2011 | Harberts et al. |
| 2013/0204318 | A1 | 8/2013 | Young |
| 2013/0238074 | A1 | 9/2013 | Zimmerling |
| 2013/0245733 | A1 | 9/2013 | Yomtov |
| 2014/0194963 | A1* | 7/2014 | Desai ............ A61L 31/06 607/116 |
| 2014/0322964 | A1 | 10/2014 | Deininger et al. |

FOREIGN PATENT DOCUMENTS

| | | |
|---|---|---|
| EP | 2656876 A1 | 10/2013 |
| EP | 2742969 A1 | 6/2014 |
| WO | 02089909 A1 | 11/2002 |
| WO | 2010055453 A1 | 5/2010 |

OTHER PUBLICATIONS

U.S. Appl. No. 14/951,237, filed by Decré, Michel Marcel José, on Nov. 24, 2015.
International Search Report and Written Opinion of International Application No. PCT/EP2015/077662, mailed Jun. 2, 2016, 7 pp.

\* cited by examiner

LEAD AND A SYSTEM FOR MEDICAL APPLICATIONS

This application claims the benefit of U.S. Provisional Application Ser. No. 62/084,311, by Young et al., and filed Nov. 25, 2014, which is incorporated herein by reference in its entirety.

TECHNICAL FIELD

The present disclosure relates, in some examples, to a lead for medical applications and a system for medical applications, such as, e.g., a lead and system configured for neurostimulation applications.

BACKGROUND

Implantable neurostimulation devices have been used to treat acute or chronic neurological conditions. Deep brain stimulation (DBS), the electrical stimulation of sub-cortical structures, belongs to this category of implantable devices, and has been shown, for example, to be therapeutically effective for Parkinson's disease, Dystonia, and Tremor. Applications of DBS in the domain of psychiatric disorders (e.g., obsessive compulsive disorder and depression) also exist.

SUMMARY

In some examples, the disclosure relates to an electrical lead and implantable medical device systems employing such electrical leads for medical applications. In one examples, the disclosure is directed to a medical device system comprising a thin film configured to be secured to at least a portion of a carrier core, wherein the thin film has a distal end, a proximal end, and at least one electrode between the proximal end and the distal end; and at least one fixation element configured to secure the distal end of the thin film to the carrier core, wherein the fixation element comprises at least one of a distal extension portion of the thin film configured to be at least partially wrapped around the carrier core distal to the at least one electrode or a jacket tube configured to be positioned around the carrier core and the thin film.

In another example, the disclosure relates to a method for forming a medical device system configured for medical applications, the method comprising securing a thin film around at least a portion of a carrier core, wherein the thin film has a distal end, a proximal end, and at least one electrode between the proximal end and the distal end; and securing the distal end of the thin film via at least one fixation element to the carrier core, wherein the fixation element comprises at least one of a distal extension portion of the thin film at least partially wrapped around the carrier core distal to the at least one electrode or a jacket tube located around the carrier core and the thin film.

In another example, the disclosure relates to a medical device system comprising an implantable medical device; and an implantable medical lead, wherein the implantable medical device is configured to at least one of deliver electrical stimulation to a patient or sense electrical activity of the patient via the implantable medical lead, wherein the implantable lead comprises a thin film configured to be secured to at least a portion of a carrier core, wherein the thin film has a distal end, a proximal end, and at least one electrode between the proximal end and the distal end; and at least one fixation element configured to secure the distal end of the thin film to the carrier core, wherein the fixation element comprises at least one of a distal extension portion of the thin film configured to be at least partially wrapped around the carrier core distal to the at least one electrode or a jacket tube configured to be positioned around the carrier core and the thin film.

The details of one or more examples are set forth in the accompanying drawings and the description below. Other features, objects, and advantages will be apparent from the description and drawings, and from the claims.

DETAILED DESCRIPTION

Figure 1:
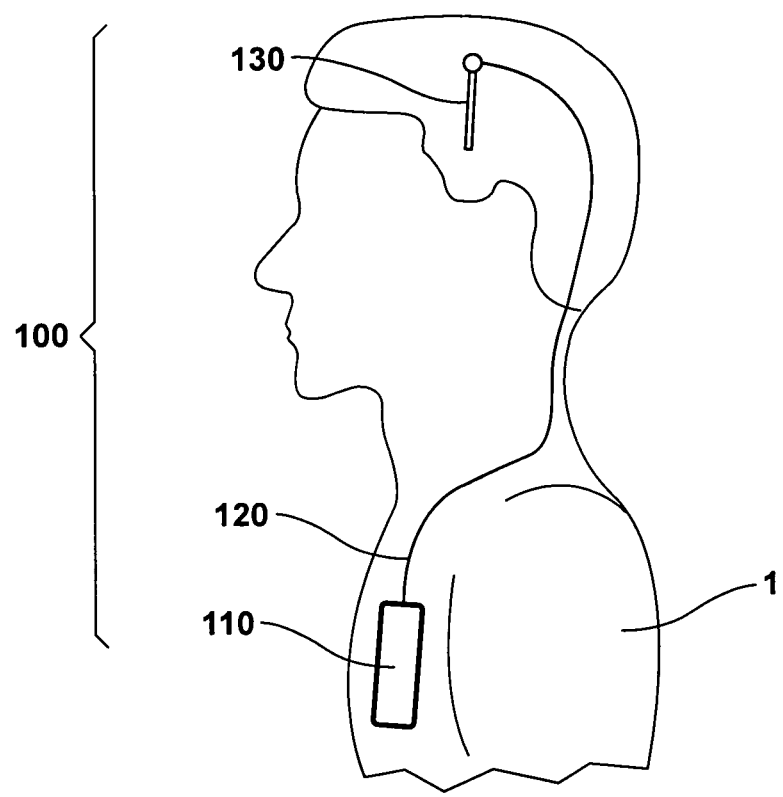
FIG. 1 is a schematic diagram illustrating an example neurostimulation system for delivery of DBS.

Electrical stimulation systems are under development with an increased number of electrodes and smaller electrodes (e.g., in order to better control the delivery of electrical stimulation) in a technology based on thin film manufacturing. These systems may include an electrical stimulation lead made from a thin film based on thin film technology, e.g., as described in PCT Application Publication WO 2010/055453 A1, to Harberts et al., entitled "Spiraled Wires in a Deep-Brain Stimulator Probe." In some examples, the electrical stimulation lead may include a multilayer thin film fixed on a carrier core, which provides mechanical strength to the thin film. These leads may have multiple electrode areas and may enhance the precision of stimulation (and/or sensing of electrical signals) to address the appropriate target in the brain and relax the specification of electrode positioning. Meanwhile, undesired side effects due to undesired stimulation of neighboring areas may be minimized. Some example leads that are based on thin film manufacturing may include, e.g., those described by U.S. Pat. No. 7,941,202, to Hetke et al., entitled "Modular Multichannel Microelectrode Array and Methods of Making Same," and U.S. Patent Application Publication No. 2011/0093052, to Anderson et al., and entitled "Neural Interface System," and have been used in research products in animal studies.

In some examples, an electrical stimulation lead may include a thin film substrate secured to a carrier core (e.g., by wrapping the thin film around at least a portion of the carrier core). The thin film substrate may include conductive tracks running within a relatively narrow strip or cable section of the thin film and broadened electrode pads at one or both ends of the cable at least partially wrapped around the carrier core. One or more electrodes at the distal end may be electrically connected to the driving electronics of the lead via the conductive tracks, and may deliver electrical stimulation pulses or other signals generated, e.g., by an implantable pulse generator. Such a configuration may be used, e.g., to provide a magnetic resonance imaging (MRI) compatible lead including an electrode array with a plurality of electrodes for DBS or other types of stimulation.

In some examples, the distal end of the thin film including the electrode array may be attached to the carrier core of the lead by an adhesive. However, using such an adhesive bonding configuration, it may be possible for the distal part of the thin film to delaminate and subsequently detach from the carrier core. In some examples, there may not be a method (e.g., either non-destructive test or process quality control test) that can provide absolute assurance of bond integrity between the carrier care and thin film. Moreover, adhesive bond failures may occur in the absence of structural loads by failure of the interface between the adhesive and the thin film. Therefore, successful strength and fatigue testing may not necessarily demonstrate bond durability because such testing may not assess the environmental resistance of the adhesive interface. Furthermore, it may be difficult to accurately predict the performance of the adhesive interface over time. Also, use of adhesive might not be desireable in such a configuration, e.g., as it may pollute/disrupt the distal surface during manufacturing and the curing of the glue may induce unwanted stresses on the distal portion.

For one or more of the above reasons, an adhesive bond between the thin film and carrier core may fail over time and the adhesive process quality is difficult to test and qualify. Thus, in some examples, a lead construction technique that relies solely on an adhesive to secure the thin film to the carrier core may be avoided. Rather, the thin film should be secured to the carrier core using one or more additional or alternative techniques. For example, the cable part of the thin film may be secured to the carrier core by applying a continuous coating on top of the thin film when wound about the carrier core and/or by clamping the thin film to the carrier, e.g., by employing additional tubing positioned over the thin film and carrier core to protect and fix the thin film to the carrier core. However, for the distal portion of the thin film, these methods may not be suitable, e.g., because the electrode surfaces on the distal portion of the thin film may need to be exposed to maintain direct contact to brain tissue when delivering electrical stimulation. In some examples, a covering of the stimulation electrodes at least negatively affects the generated stimulation field or completely blocks the stimulation field and thus should be avoided.

In some examples, it is therefore an object of the present disclosure to improve a lead and a system for medical applications, especially in that the fixation of the distal end of the thin film of a lead for medical applications is improved. In some examples, the object is solved with a lead and a system for medical applications, where the distal end of the thin film is secured to the carrier core by mechanical attachment rather than solely based on adhesive bonding.

In accordance with one or more examples of the disclosure, an electrical lead for medical applications may comprise a carrier core, a thin film secured around the carrier core, (e.g., by wrapping the thin film around the carrier core one or more times in a coiled fashion), wherein the thin film has a distal end and proximal end; and at least one fixation element configured to secure the distal end of the thin film to the carrier core, wherein the fixation element comprise at least one of a distal extension portion of the thin film at least partially wrapped around the carrier core or a jacket tube located around the carrier core and the thin film.

In some examples, the fixation element may be at least partially formed by a distal extension of the thin film itself. By this, the advantage may be achieved that the structure of the thin film may be used to provide at least a part of the fixation element which secures the thin film to the carrier core. In some examples, no further structural element may be needed to secure the thin film to the carrier core.

In some examples, the distal extension portion of the thin film may be spirally wrapped at least a full loop around the carrier of the lead to secure the thin film, particularly the distal portion, to the carrier core. In another example, the distal extension portion of the thin film may be spirally wrapped less than a full loop around the carrier core of the lead.

In some examples, the thin film may have a stimulation electrode section, wherein the fixation element is formed by a distal extension portion of the thin film distal to the stimulation electrode section of the thin film, and wherein the distal extension portion forms the distal end of the thin film. The distal extension portion may be an extension flap or an extension strip and may not include metal track or other electrically conductive tracks that may be found in the stimulation electrode section of the thin film.

By providing a distal extension portion distal to the stimulation electrode section, it is possible that a further fixation mechanism may be employed, e.g., an outer coating or outer tube, that covers the distal extension portion of the thin film to at least partially secure the thin film to the carrier core, e.g., to prevent detachment and delamination of the distal portion of the carrier core. Since it may not be possible to provide a further fixation upon the thin film in the stimulation electrode section without covering the stimulation electrodes, e.g., by providing a topmost layer covering at least partially the thin film, the distal extension portion creates an advantageous possibility to provide and to attach a further fixation upon the thin film distal to the stimulation electrode section without covering the stimulation electrodes.

In some examples, the distal extension portion may be at least partially covered by a coating and/or by an additional fastener, e.g., a tube such as a heat shrink tube, to further secure the thin film to the carrier core. The coating may be an adhesive or a polymer. This additional fixation may be provided relatively easily and may be relatively effective at the same time. In some examples, such a topmost fixation may be visible and, thus, the correct fixation may be inspected easily with non-destructive inspection methods.

In some examples, the stimulation electrode section may be a broadened thin film section, e.g., in term of width of the thin film. In this manner, several electrodes may be arranged side by side on the surface of the thin film, especially so as to form a complex electrode array, e.g., having electrodes at various axial positions of the lead and at various angular positions around the circumference of the lead. In some examples, the broadened thin film section may be quadrangular and may have, e.g., a rectangular or a rhomboid shape.

In some examples, the broadened thin film section may be arranged asymmetrically to at least one adjacent section of the thin film. By this, the wrapping of the broadened thin film section around the carrier core may be improved in addition to the wrapping of an adjacent section of the thin film. The adjacent section may be, e.g., the distal extension portion.

The thin film may also have a cable section between the proximal end and the distal end of the thin film, where the stimulation electrode section may be connected to the cable section of the thin film and the distal extension. The stimulation electrode section may be secured to the carrier core in part by the adjacent cable section, e.g., by wrapping the cable section of the thin film around the carrier core, in addition to the distal extension being wrapped or otherwise secured distal to the stimulation electrode section. In this manner, a stable and reliable fixation may be provided at the distal end and proximal end of the stimulation electrode section.

In some examples, the cable section may at least be partially covered by a coating and/or by an additional fastener, e.g., a tube such as a heat shrink tube. The coating may be an adhesive or a polymer. Likewise, the coating and/or additional fastener may also cover the distal extension portion but not the stimulation electrode section. Such a configuration provides an additional fixation upon the cable section of the thin film, which at the same time may be very effective. In some examples, such a top most fixation may be visible and, thus, the correct fixation may be inspected easily with non-destructive inspection methods.

Alternatively or additionally, the distal end of the thin film may be at least partially fixed to the carrier by twining and/or braiding, especially wherein the thin film comprises twining and/or braiding extensions. By this, a stable and reliable fixation may be provided, for example, for the stimulation electrode section. In particular, it is possible that the twining and/or braiding extensions are arranged adjacent to or along or around the stimulation electrode section.

Furthermore, the fixation element may comprise or may be a jacket tube. The jacket tube may be placed above and upon the distal end of the thin film, and secure the thin film to the carrier core. It is possible that the jacket tube is arranged above and upon the stimulation electrodes section of the thin film. The jacket tube may prevent a dislocation of the thin film, especially the distal end of the thin film. Also, a dislocation of the distal stimulation electrode with the stimulation electrode array may be prevented.

In some examples, the jacket tube does not obstruct the direct contact between the stimulation electrodes and the tissue surrounding the distal end of the lead, when the lead is implanted into tissue, e.g. brain tissue. For example, the jacket tube may have a fine meshed structure. In this manner, the advantage is achieved that the jacket tube does not obstruct the direct contact between the stimulation electrodes and the tissue surrounding the distal end of the lead. Any stimulation field generated by the stimulation electrodes may directly affect the surrounding tissue. In case of a fine meshed jacket tube, the tube may have fine wires and have a high aspect ratio, large openings area and a small filled area to provide good accessibility of brain tissue to the electrode surface. At least a substantial portion of the electrode may remain uncovered. In some examples, the jacket tube may be formed of a substantially non-electrically conductive material, e.g., to prevent conduction of stimulation from the electrode surface through the jacket tube.

In some examples, the jacket tube may have apertures formed in the body of the tube which are sized, shaped, and arranged based on the electrode array of the stimulation electrode section. For example, the apertures may be substantially the same shape and size (or larger) as the electrodes on the stimulation electrode section, and arranged according to the arrangement of the stimulation electrodes, e.g., so that the stimulation electrodes may be exposed through such apertures. For example, the jacket tube may be positioned over the stimulation electrode section of the thin film such that the apertures may be substantially aligned to the electrodes in the distal electrode array and the apertures in the jacket leave the electrode area uncovered.

Some examples of the present disclosure relate to a system for medical applications, e.g., a system for neurostimulation and/or sensing of electrical signals of the patient. The system for medical applications, (e.g., for neural applications including neural stimulation or deep brain stimulation) comprises at least one lead as described herein. The system may comprise all structural and functional features and also one or more of the advantages described herein in connection with the lead according to the present disclosure and its possible embodiments.

FIG. 1 a schematic diagram illustrating an example neurostimulation system 100 for delivery of deep brain stimulation (DBS). As shown, the neurostimulation system 100 may include implantable medical device (IMD) 110 (also referred to in some examples as an implantable pulse generator device (IMD) or controller) that may be surgically implanted in the chest region of a patient 1, e.g., below the clavicle or in the abdominal region of a patient 1. The IMD 110 may be configured to generate and supply the necessary voltage pulses or other suitable type of electrical stimulation for delivery to patient 1 via DBS probe 130. Neurostimulation system 100 may further include an lead extension 120 connected to the IMD 110 and running subcutaneously to the skull of patient 1, e.g., along the neck, where it terminates in a connector (not shown). A DBS lead arrangement 130 may be coupled to the connector and to the lead extension and implanted in the brain tissue of patient 1, e.g., through a burr-hole in the skull.

Figure 2A:
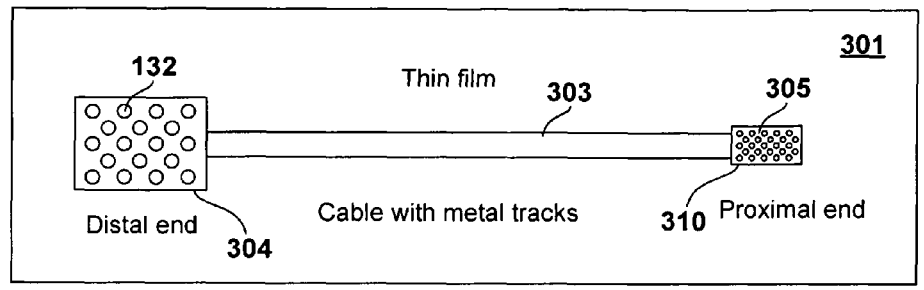
FIGS. 2A-2C are schematic diagrams illustrating various components of an example probe of a neurostimulation system for DBS.
Figure 2B:
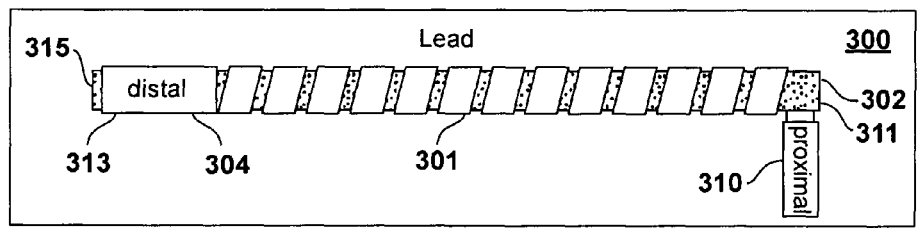
Figure 2C:
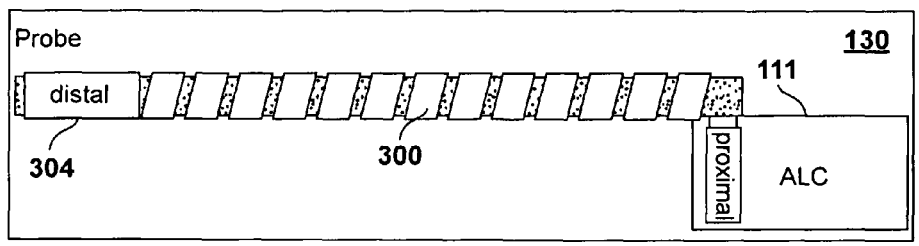

FIGS. 2A-2C are schematic diagrams illustrating example architecture for DBS probe 130 and other components of system 100. As shown, DBS probe 130 includes DBS lead 300 and active lead can (ALC) 111. Lead 300 comprises thin film 301 wound around carrier core 302. Carrier core 302 may provide the mechanical configuration of DBS lead 300 and thin film 301. Thin film 301 may include at least one electrically conductive layer, preferably made of a biocompatible material. Thin film 301 may be secured to carrier core 302 by wrapping thin film 301 around carrier core 302 and further processed to form lead 300. Thin film 301 for lead 300 may be formed by a multilayer thin film product including distal end 304, cable 303 with electrically conductive tracks (e.g., metal tracks) and proximal end 310.

Carrier core 302 may have any suitable configuration. In some examples, carrier core 302 may be an elongated member having a circular cross-section, although other cross-sections are contemplated, such as, e.g., square or hexagonal. Carrier core 302 may be a solid member or have a hollow core. In some examples, it is preferred that carrier core 302 be relatively stiff during implantation but able to flex or bend to some degree after implantation. The hollow core may allow for the insertion of a stiffening member such as a stylet into the hollow core, e.g., during implantation of lead 300. Carrier core 302 may be configured to not substantially shrink, stretch, or compress during and/or after implantation.

In some examples, carrier core 302 should be flexible and have a good rotational torque transfer, e.g., in instances of permanent (chronic) implant of lead 300. Some acute applications may have a different set of preferences. For instance, in acute implantation, no burr-hole devise may be used and flexibility and limited compressibility are of less concern.

Carrier core 302 may be formed of any suitable material including silicone, titanium, and/or polyether ether ketone (PEEK) based materials. For the mechanical requirements as mentioned above, other polymers can be more useful e.g. bionate. In addition, metal tubes (e.g., laser machined to bendable chains) may be used. In acute applications, a solid metal may be used for carrier core 302. In acute application, there may not be a need for carrier core 302 to be hollow or flexible. In chronic applications, carrier core 302 is implanted with a stiffener inside. After implantation, the stiffener may be removed.

Distal portion of lead 300 may have a diameter between about 0.5 millimeters (mm) and about 3 mm diameter, e.g., about 1.3 mm. The diameter of lead 300 may be defined by the diameter of carrier core 302 in combination with the thickness of thin film 301 and any coating applied over carrier core 302 and/or thin film 301. The proximal portion of lead 300 (the portion adjacent to ALC 111) may have a diameter between about 0.5 mm and about 4 mm diameter. The length of lead 300 may be about 10 centimeters (cm) to about 20 cm, e.g., about 15 cm, and may vary based on the particular application, e.g., acute versus chronic implantation. Other dimensions than those examples described herein are contemplated.

As shown, proximal end 310 of thin film 301 may be arranged at proximal end 311 of lead 300. Proximal end 310 of thin film 301 may be connected to the active lead can 111. For example, active lead can 111 may be electrically coupled to array of electrodes 132 on distal end 304 of thin film 301, which is arranged at distal end 313 and next to distal tip 315 of the DBS lead 300. The active lead can 111 comprises the switch matrix of the DBS steering electronics. The distal end 304 comprises array of electrodes 132 for the brain stimulation. The proximal end 310 comprises the interconnect contacts 305 for each electrically conductive track in the cable 303. The cable 303 comprises a plurality of electrically conductive tracks to connect each distal electrode 132 to a designated proximal contact 305. Distal end 313 of lead 300 may be the end of lead 300 which is the remote end of the lead with regard to the body surface when implanted in a patient. In particular, in case of a lead for brain applications, distal end 313 of lead 300 may be the end of lead 300 which is remote to the burr-hole of the skull through which lead 300 is implanted, and embedded within the brain tissue.

In some examples, electrodes 132 may form a complex electrode array. Such a configuration may be helpful, e.g., to create a stimulation field that is adapted to and conforms to the target stimulation region. A complex electrode array may generally refer to an arrangement of electrodes at multiple non-planar or non-coaxial positions, in contrast to simple electrode array geometries in which the electrodes may share a common plane or common axis. An example of a simple electrode array geometry may be an array of ring electrodes distributed at different axial positions along the length of the lead. An example of a complex electrode array geometry, in accordance with this disclosure, may be an array of electrodes positioned at different axial positions along the length of the lead, as well as at different angular positions about the circumference of the lead.

As described above, lead 300 may be formed by wrapping thin film 301 around carrier core 302. Micromachining technology such as thin film technologies to manufacture thin film 301 may enable the realization of smaller electrodes. Again, the multilayer lead structure may be used in medical devices like active implantable devices such as, e.g., implantable neurostimulation devices. For example, lead 300 may be employed in an implantable neurostimulation device in the form of a deep brain stimulation system.

Thin film structures may provide an advantage in that a relatively small structure can be built with thin film technology. A thin film may be a layer or multilayer structure of material ranging from fractions of a nanometer (monolayer) to several micrometers in thickness. Electronic semiconductor devices and optical coatings are applications benefiting from thin-film construction. Thin film technology and thin film manufacturing processes may allow the manufacturing of leads for medical purposes such as neurostimulation leads like, e.g., deep brain stimulation leads with diameters of less than 2 mm, for example 0.75 mm to 1.50 mm and a plurality of electrodes (e.g., approximately 10 electrodes or greater, preferably approximately 20 electrodes or greater, preferably approximately 40 electrodes or greater).

Although not shown in FIGS. 2A-2C, in some examples, thin film 301 may include a distal extension portion, e.g., located distal to the portion of thin film 301 including electrodes 132. In some examples, the distal extension portion may not include any metal track or other conductors coupled to any electrodes in lead 300, including electrodes 132. The distal extension portion may be at least partially wrapped around carrier core 302 to secure thin film 301 to core 302, particularly at or proximate to distal end 304. Additionally or alternatively, lead 300 may include a jacket tube positioned over at least a portion of thin film 301 including electrodes 132 and carrier core 302 to secure thin film 301 to core 302, particularly at or proximate to distal end 304.

Figure 3:
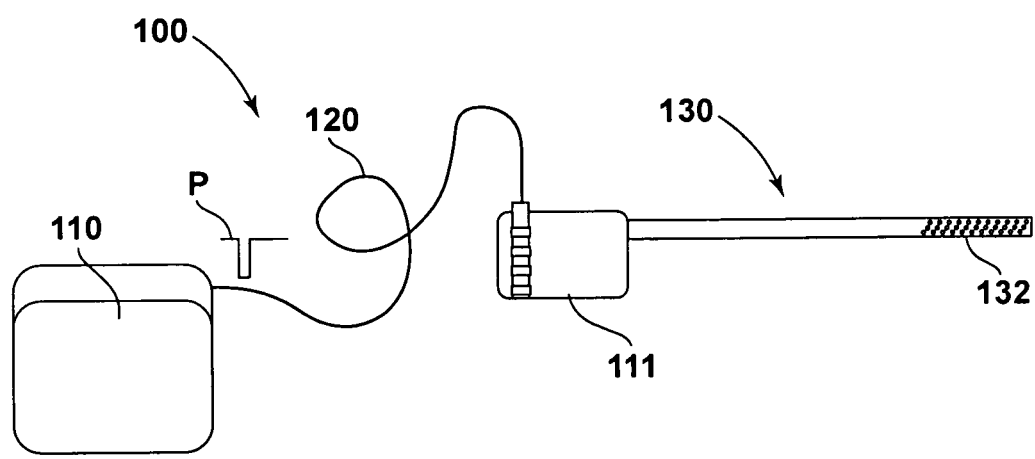
FIG. 3 is a schematic diagram illustrating the example probe system of FIG. 1.

FIG. 3 shows schematically and in greater detail an embodiment of a system 100 for brain applications, here for neurostimulation and/or neurorecording as a deep brain stimulation system 100 as shown in FIGS. 1 and 2A-2C. System 100 comprises at least one DBS probe 130 for brain applications with stimulation and/or recording/sensing electrodes 132, wherein, e.g., an array of forty total electrodes 132 may be located on an outer body surface at the distal end of the DBS probe 130. By way of the extension wire 120, electrical stimulation, such as, e.g., pulses P, supplied by IMD 110 may be transmitted to active lead can 111. The electrical stimulation may be transmitted from active can lead 111 to array of electrodes 132 to deliver the electrical stimulation to a target tissue in the brain of patient 1.

In some examples, the systems, device, and articles described herein, e.g., system 100, lead 300, and probe 130 may be configured substantially the same or similar to the examples described in U.S. Patent Application Publication No. 2013/0204318, to Young, entitled "Thin Film for a Lead for Brain Applications. The entire content of the U.S. Patent Application Publication No. 2013/0204318 is incorporated herein by reference in its entirety.

In some example systems, DBS lead 300 includes four 1.5 mm-wide cylindrical electrodes at the distal end spaced by about 0.5 mm or about 1.5 mm apart from one another. Cylindrical electrodes are sometimes referred to as ring electrodes. The diameter of lead 300 may be about 1.27 mm and the conductive material (e.g., metal) used for electrodes 132 and the interconnect wires (not shown) may be an alloy of platinum and iridium. The coiled interconnect wires may be insulated individually by fluoropolymer coating and protected in an 80 micron thick urethane tubing. With such an example electrode design, the current distribution may emanate uniformly around the circumference of the electrode, which leads to electrical stimulation of all areas surrounding the electrode.

In other examples, the electrodes may form an array of electrodes with a complex electrode array geometry that is capable of producing shaped electrical fields. An example of a complex electrode array geometry may include an array of electrodes positioned at different axial positions along the length of a medical lead, as well as at different angular positions about the periphery, for example, circumference, of the medical lead. The complex electrode array geometry may include multiple electrodes (e.g., partial ring or segmented electrodes) around the perimeter of each medical lead 20. In other examples, the complex electrode array geometry may include electrode pads distributed axially and circumferentially about the medical lead. In either case, by having electrodes at different axial and angular positions, electrical stimulation may be directed in a specific direction from probe 130 to enhance therapy efficacy and reduce possible adverse side effects from stimulating a large volume of tissue. In some examples, the array of electrodes may be combined with one or more ring electrodes on probe 130.

Figure 16:
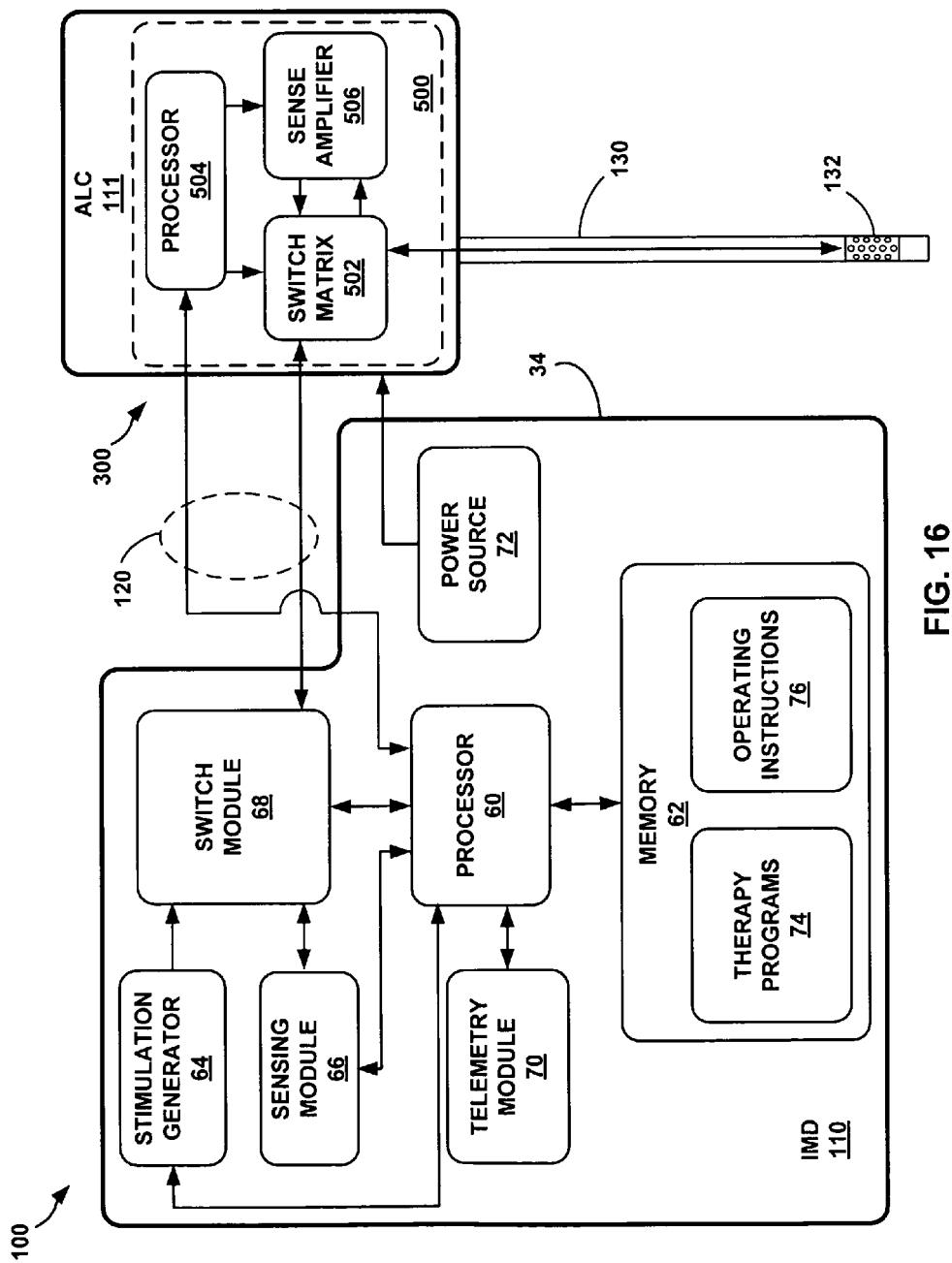
FIG. 16 is a a functional block diagram illustrating components of an example medical device system including an implantable medical device and a separate active lead can (ALC) with a switch matrix to direct signals from the implantable medical device to different electrodes.

FIG. 16 is functional block diagram illustrating components of an example therapy system 100 including IMD 110 and ALC 111. In the example shown in FIG. 2, IMD 110 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 110 to perform various functions described herein.

In the example shown in FIG. 2, memory 62 stores therapy programs 74 and operating instructions 76, for example, in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width, and pulse rate of a stimulation signal. The stimulation signals delivered by IMD 110 may be of any form, such as stimulation pulses, continuous-wave signals (e.g., sine waves), or the like. Operating instructions 76 guide general operation of IMD 110 under control of processor 60, and may include instructions for monitoring brain signals within one or more brain regions via electrodes 132 and delivering electrical stimulation therapy to patient 12.

Stimulation generator 64, under the control of processor 60, generates stimulation signals for delivery to patient 12 via selected combinations of electrodes 132. In some examples, stimulation generator 64 generates and delivers stimulation signals to one or more target regions of brain 28 (FIG. 1), via a select combination of electrodes 132, based on one or more stored therapy programs 74. Processor 60 selects the combination of electrodes 132 with control signals to processor 504 of ALC 111. In turn, processor 504 of ALC 111 selectively activates active switch matrix 504 to direct the stimulation signals received from stimulation generator 64 to the selected electrodes 132. The stimulation parameter values and target tissue sites within brain 28 for stimulation signals or other types of therapy may depend on the patient condition for which therapy system 100 is implemented to manage.

The processors described in this disclosure, including processor 60 and processor 504, may include one or more digital signal processors (DSPs), general-purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more therapy programs.

Processor 60 may control switch module 68 to select stimulation generator 64 or sensing module 66. In turn, processor 60 directs processor 504 of electronic module 500 to apply the stimulation signals generated by stimulation generator 64 to selected combinations of electrodes 132, or to sense signals from selected combinations of electrodes 132 via sense amplifier 506 of electronic module 500. In particular, active switch matrix 502 of electronic module 500 may couple stimulation signals to selected conducting tracks within probe 130, which, in turn, deliver the stimulation signals to selected electrodes 132. Hence, although there may be many, for example, 40, electrodes, active switch matrix 502 may select a subset of one, two or more electrodes for delivery of stimulation pulses. Active switch matrix 502 may be a switch array, an array of one or more transistors such as Field-Effect Transistors (FETs), switch matrix, multiplexer and/or demultiplexer, or any other type of switching module configured to selectively couple stimulation energy to selected electrodes 132 and to selectively sense bioelectrical brain signals with selected electrodes 132. Hence, stimulation generator 64 is coupled to electrodes 132 via switch module 68, conductors within cable 120 between IMD 110 and ALC 111, active switch matrix 502, and conducting tracks within probe 130. Additionally, the logic path between stimulation generator and electrodes 132 may include one or more discrete components such as capacitors, resistors, logic gates, transistors, and the like. Thus, it will be understood that when reference is made to coupling of stimulation generator 64 or other components of IMD 110 to electrodes 132, this refers to the enabling of a logic path between the logic components so that signals may be transferred there between, and is not intended to necessarily require a direct electrical coupling of the components.

In some examples, IMD 110 does not include switch module 68 and all switching functions may be performed by active switch matrix 502. For example, IMD 110 may include multiple sources of stimulation energy (e.g., current sources). Additionally or alternatively, a stimulation generator similar to stimulation generator 64 may reside within ALC (not shown) and may generate the stimulation pulses that are routed to electrodes 132 via active switch matrix 502. In such cases, the stimulation generator within the ALC may receive power from power source 72 and may receive control signals from stimulation generator 64 or other logic of IMD 110. The stimulation generator in ALC may be provided in addition to, or instead of, stimulation generator 64 of IMD 110. Thus, electronics for driving probe 130 and electrodes 132 of lead may reside in IMD 110, ALC 111, or some combination thereof. Stimulation generator 64 and/or a stimulation generator residing within ALC 111 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses at a given time via multiple electrode combinations. In some examples, however, stimulation generator 64 and active switch matrix 502 may be configured to deliver multiple channels of stimulation on a time-interleaved basis. For example, active switch matrix 502 may serve to time divide the output of stimulation generator 64 across different electrode combinations at different times to deliver multiple programs or channels of stimulation energy to patient 12. In another example, system 100 may not include ALC 111 between IMD 110 and probe 130. In such an example, the entire functionality attributed to the combination of IMD 110 and ALC 11 may be performed by components of IMD 110.

Sensing module 66, under the control of processor 60, is configured to sense bioelectrical brain signals of patient 12 via active switch matrix 502, sense amplifier 506, and a selected subset of electrodes 132 or with one or more electrodes 132 and at least a portion of a conductive outer housing 34 of IMD 110, at least a portion of a conductive outer housing of ALC 111, an electrode on outer housing 34 of IMD 110, an electrode on an outer housing of ALC 111, or another reference. Processor 60 may control switch module 68 and/or switch matrix 502 to electrically connect sensing module 66 to selected electrodes 132 via active switch matrix 502 and sense amplifier 506 of ALC 111. In this way, sensing module 66 may selectively sense bioelectrical brain signals with different combinations of electrodes 132.

Telemetry module 70 is configured to support wireless communication between IMD 110 and an external programmer (not shown) or another computing device under the control of processor 60. Processor 60 of IMD 110 may receive, as updates to programs, values for various stimulation parameters from an external programmer via telemetry module 70. The updates to the therapy programs may be stored within therapy programs 74 portion of memory 62. Telemetry module 70 in IMD 110, as well as telemetry modules in other devices and systems described herein, such as an external programmer, may accomplish communication by RF communication techniques. In addition, telemetry module 70 may communicate with an external medical device programmer via proximal inductive interaction of IMD 110 with the programmer. Accordingly, telemetry module 70 may send and receive information to/from an external programmer on a continuous basis, at periodic intervals, or upon request from IMD 110 or the programmer.

Power source 72 delivers operating power to various components of IMD 110. Power source 72 may include a small rechargeable or non-rechargeable battery and a power generation circuit to produce the operating power. Recharging may be accomplished through proximal inductive interaction between an external charger and an inductive charging coil within IMD 110. In some examples, power requirements may be small enough to allow IMD 110 to utilize patient motion and implement a kinetic energy-scavenging device to trickle charge a rechargeable battery. In other examples, traditional batteries may be used for a limited period of time.

Figure 4:
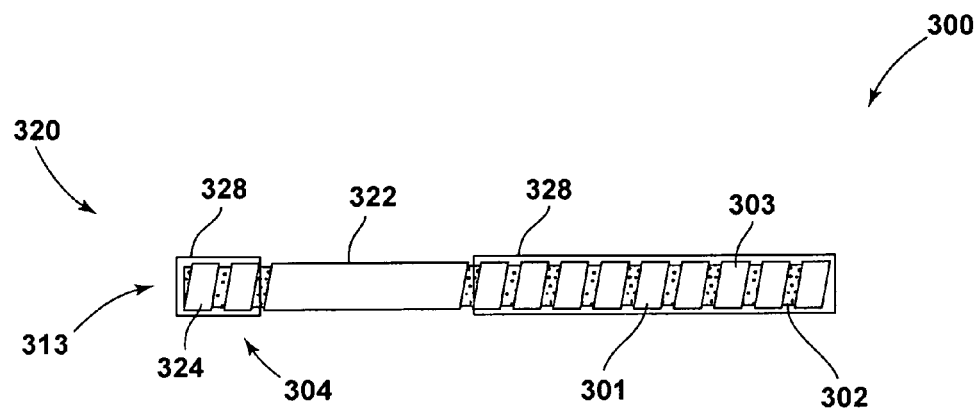
FIG. 4 is a schematic diagram illustrating a distal portion of a lead according to a first example.
Figure 5:
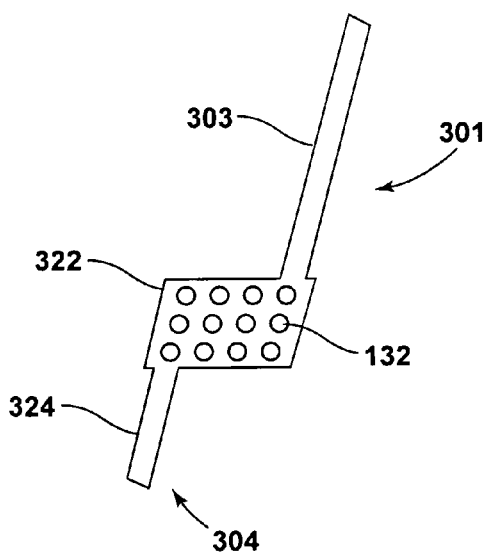
FIG. 5 is a schematic diagram illustrating the distal end of the thin film according to the example of FIG. 4.

FIG. 4 is a schematic diagram illustrating lead 300 according to a first example. FIG. 5 is a schematic diagram illustrating thin film 301 according to the example of FIG. 4 shown from above prior to being wrapped around carrier core 302. In FIGS. 4 and 5, the illustrated components of thin film 301 include cable section 303, stimulation electrode section 322, and distal extension portion 324. As shown in FIG. 5, the stimulation electrode section 322 is a thin film section that is broadened in the width direction compared to that of cable section 303 and distal extension portion 324, and the broadened thin film section is arranged asymmetrically to the longitudinal axis of the adjacent sections 303, 324 of the thin film 301.

As shown, stimulation electrode section 322 of the thin film 301 is located distal to cable section 303 of the thin film 301. Stimulation electrode section 322 of the thin film 301 includes an array of stimulation electrodes 132. Thin film 301 also include distal extension portion 324 of the thin film 301, which is connected to stimulation electrode section 322 and cable section 303. In such a configuration, thin film 301 includes cable section 303 on one side of stimulation electrode section 322 and distal extension portion 324 on the other side. Distal extension portion 324 forms the most distal part of the thin film 301. Distal extension portion 324 does not include any electrodes.

Thin film 301 may be wrapped around carrier core 302. For example, both cable section 303 of the thin film 301 and distal extension portion may be wrapped around carrier core 302 such that portions of thin film 301 are wrapped around carrier core 302 on either side of stimulation electrode section 322. In some examples, stimulation electrode section 322 may be folded around carrier core 302, e.g., such that the opposite ends of stimulation electrode section 322 are adjacent to each other around carrier core 302 but do not substantially overlap.

In some examples, without distal extension portion 324, the fixation of the stimulation electrode section 322 to carrier core 302 may rely solely or partially on adhesive forming an adhesive bond between the opposing surfaces of carrier core 302 and stimulation electrode section 322. As noted above, use of adhesive may not be desirable in this part of the system, e.g., as it might pollute/disrupt the distal surface during manufacturing and the curing of the glue adhesive may induce unwanted stresses on the distal surface/portion of lead 300. However, in the example of FIGS. 4 and 5, the proximal side of the stimulation electrode section 322 may be secured to carrier core 302 by wound cable section 303 and the distal side of the stimulation electrode section 322 may be secured to carrier core 302 by wrapped distal extension portion 324. Thus, the stimulation electrode section 322 is secured by wrapping thin film 301 at both sides (distal and proximal) of stimulation section 322 around the carrier 302 by the combination of cable section 303 and distal extension portion 324. By applying these wrapped extensions (the cable section 303 and the distal extension portion 324) at both sides of the stimulation electrode section 322, the stimulation electrode section 322 may be fixed to carrier core 302 by fixation elements in addition to, or as alternatives to, the use of adhesive to bond stimulation electrode section 322 to carrier core 302 only. Distal extension portion 324 may be secured to the core by adhesive. Moreover, a cover coating or jacket tube (328) may be applied to secure the fixation of the thin film to the core Distal extension portion 324 may be formed from substantially the same material as stimulation electrode section 322 and cable section 303. However, distal extension portion 324 forms the most distal part of the thin film 301, and there are no other electrodes beyond stimulation electrode section 132. In some examples, distal extension portion 324 may not include any conductive portions electrically connected to the metal tracks in stimulation electrode section 322 and cable section 303, which are used to conduct electrical signal across stimulation electrodes 132. In some examples, distal extension portion 324 may comprise, consist of, or consist essentially of a polymer, such as, e.g., a medical grade polymer. For example, the medical polymer may be at least one of a polymer referred to under the trade name of Parylene (e.g., Parylene-C), SU-8, silicone, polyimide, or polyurethane. These polymers may be used when the polymer might be exposed during use to tissue, e.g. when the multilayer structure is implanted into a mammalian body.

Distal extension portion 324 may have a thickness of approximately 5 microns to approximately 50 microns, and a length extending from stimulation electrode section 324 approximately 0.2 centimeters to approximately 20 centimeters. However, other dimensions are contemplated. In some examples, the length of distal extension portion 324 may be selected relative to the diameter of carrier core 302 such that distal extension portion 324 at least partially, e.g., completely, wraps at least once around body of carrier core 302.

In some examples, cable section 303 and/or distal extension 324 may be subsequently fixed to carrier core 302 by a coating and/or outer tubing 328 over portions of cable section 303 and/or distal extension 324 around carrier core 302 to further secure stimulation electrode section 322 and a remainder of thin film 301 to carrier core 302. In some examples, the length of distal extension portion 342 may be such that, when wrapped around core 302, an amount of distal extension portion 342 may be coated and/or engaged by outer tube 328 to further secure distal extension portion 342 to carrier core 302.

With such a method of manufacturing, a lead 300 for medical applications is provided comprising at least one carrier 302 and at least one thin film 301 secured to carrier core 302, e.g., via wrapping around the carrier core 302, wherein the thin film 301 has a distal end 304 and proximal end 310, wherein the lead 300 further comprises at least one fixation element 320 for fixing the distal end 304 of the thin film 301, wherein the fixation element 320 is configured such that it forms a clamp or at least a part of a tube to prevent a delamination or detaching of the distal end 304 of the thin film 301. For example, distal extension portion 324 of about 4 mm in length may result in one full loop on carrier core 302 with a 1.2 mm diameter, which may give sufficient "grip" of distal extension portion 324 for an outer shrink tube 328 to serve as an additional fastener.

In some examples, outer tube 328 may be a medical grade shrink tube. Medical grade shrink tubes are available in a wide range of material classes including, e.g., polyvinylidene fluoride, non-phthalate, polyvinylchloride, polyester or the like. In other examples, outer tube 328 may be a silicone tube with silicone swelling agents that expand the silicone to a desired dimension, which may then allow the silicone tube to easily go over distal extension 324 wound on carrier core 302. Once the silicone tube is in place, the solvent evaporates and the silicone tube returns to its original size, thus creating a tight-seal attachment of distal extension portion 324 of thin film 301 to carrier 302.

Alternatively or additionally, distal extension portion 324 and/or cable section 303 may be covered by a coating 326, e.g., an adhesive coating. For example, adhesives may be, e.g., epoxy based, silicone based or a polymer with a polyurethane backbone. In case of tubing, additional fixation of the thin film 301 within the tubing may be realized by, e.g., filling the cavity between the film, carrier 302 and tubing with an adhesive. With e.g. epoxy adhesive all around the tube outer surface, an additional protective and securing epoxy tube may be created.

In some examples, one or more advantages may be achieved by this example design of the distal end of the lead 300. For example, the fixation of the distal end 304 of the thin film 301 may not only be based on the adhesive but also ensured by an additional structural element, e.g., the fixation element 320, which may provide additional structural support and fixation to any glued fixation. As another example, stimulation electrode section 322 may not be covered, e.g., by a topmost layer or tube, but secured by the adjacent sections 303, 324 of thin film 301. These sections 303 and 324 may be covered by additional fixation coatings or fasteners so as to prevent delamination and detaching of the cable section 303 and the distal extension 324, whereas the stimulation electrodes 132 being arranged within the stimulation electrode section 322 may remain uncovered. Thus, in some examples, it may be advantageously possible to prevent a delamination or detaching of the distal end 304 of the thin film 301 without influencing the stimulation field generated by the stimulation electrodes 132.

Figure 6:
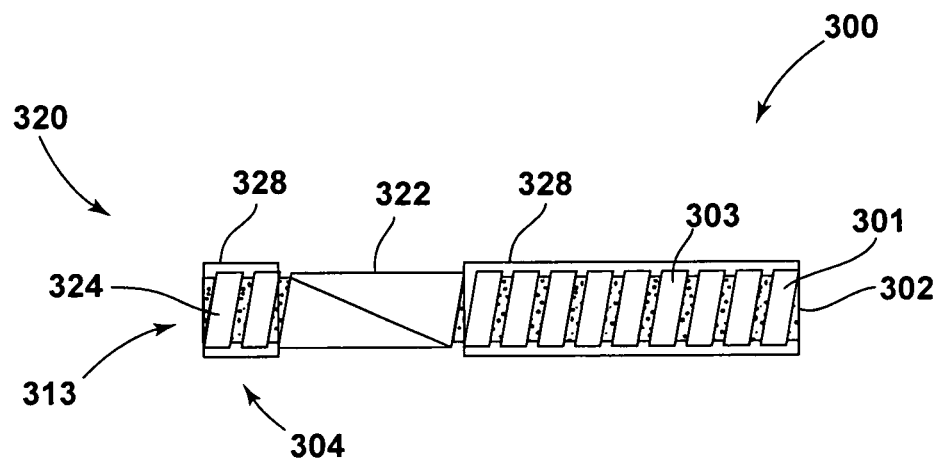
FIG. 6 is a schematic diagram illustrating a distal end of a lead according to a second example.
Figure 7:
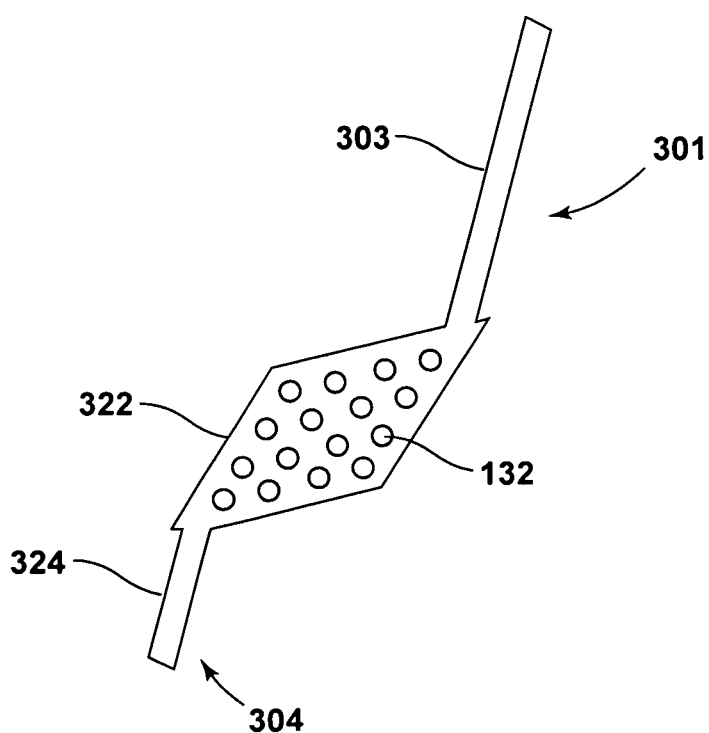
FIG. 7 is a schematic diagram illustrating the distal end of the thin film according to the example of FIG. 6.

FIG. 6 is a schematic diagram illustrating lead 300 according to a second example. FIG. 7 is a schematic diagram illustrating thin film 301 according to the example of FIG. 6 shown from above prior to being wrapped around carrier core 302. The second example may be substantially the same or similar to that of the first example shown in FIGS. 4 and 5.

However, according to the second example, the shape of stimulation electrode section 322 is different from that shown in FIG. 5. For example, as shown in FIG. 6, stimulation electrode section 322 is a rhomboid broadened thin film section and the broadened thin film section is arranged asymmetrically to the adjacent sections 303, 324 of the thin film 301. In such a configuration, when stimulation electrode section 322 is extended around carrier core 302, the opposing sides of section 322 meet along interface 327 extending along an axis that is not parallel to the longitudinal axis. The overall structure may be further secured by configuring stimulation electrode section 322 so that it is not just folded around the carrier 302, but so that the electrode array itself is spirally wound around the carrier core 302. In some examples, half a turn of stimulation electrode section 322 around carrier core 302 may provide a much increased resistance against detaching of the stimulation electrode section. In particular, in combination with the distal extension 324 as described herein, reliability improvement of the distal portion may be achieved.

Figure 8:
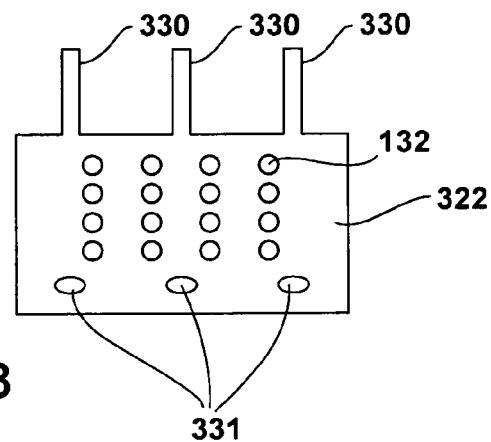
FIG. 8 is a schematic diagram illustrating a stimulation electrode section of a thin film according to a third example.

FIG. 8 is a schematic diagram illustrating stimulation electrode section 322 of thin film 301 according to a third example of the present disclosure. As shown, thin film 301 comprises extensions in the form of twining and braiding extensions 330 and one or more corresponding openings in the thin film forming twining holes 331 on the opposite side of electrodes, which can be fixed in twining holes 331. In such a configuration, stimulation electrode section 322 may be further wrapped around carrier core 302 such that extensions 330 may be fed through twining holes 331 and then secured within holes 331 to secure electrode section 322 to core 302. In some examples, extensions 330 may be braided, twinned, woven, and the like to secure extensions 330 in twining holes 331 and/or around carrier core 302. In the example shown, there are extensions 330 on opposite edges relative the array of electrodes 132 and another extension 330 between the edge extensions. In this manner, when braided, twined, and/or attached in twining holes 331, the configuration may provide for suitable attachment of electrodes section 322 when wrapped around carrier core 302.

Figure 9:
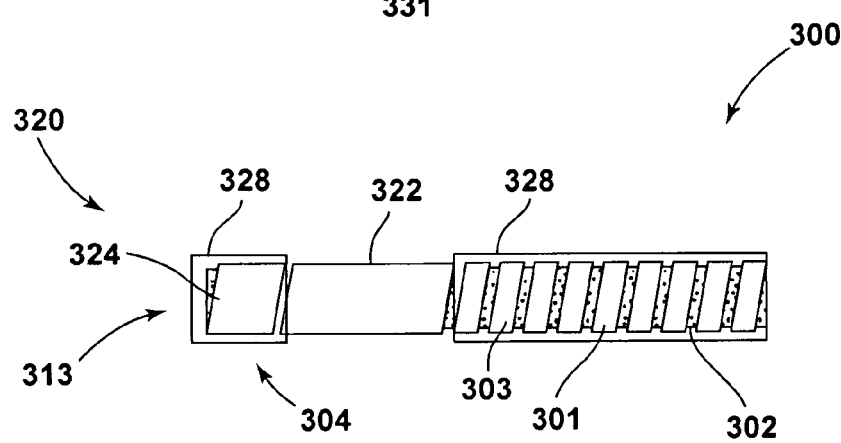
FIG. 9 is a schematic diagram illustrating a distal end of a lead according to a fourth example.
Figure 10:
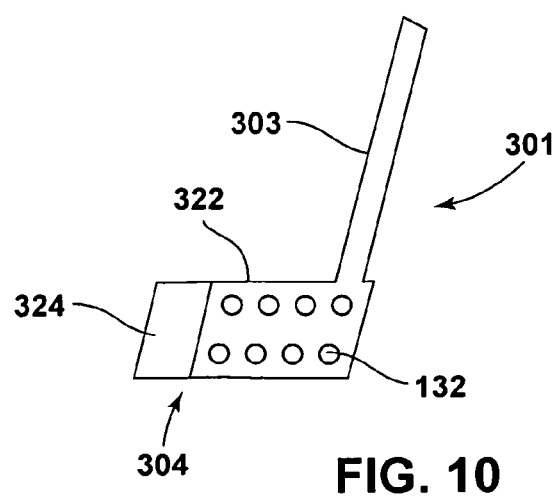
FIG. 10 is a schematic diagram illustrating the distal end of the thin film according to the example of FIG. 9.

FIG. 9 is a schematic diagram illustrating lead 300 according to a fourth example. FIG. 10 is a schematic diagram illustrating thin film 301 according to the example of FIG. 9 shown from above prior to being wrapped around carrier core 302. The fourth example may be substantially the same or similar to that of the first example shown in FIGS. 4 and 5.

However, unlike distal extension portion 324 in the form a relatively thin, cable-like extension of the first example, in the fourth example, distal extension portion 324 in the examples of FIGS. 9 and 10 has a width that is approximately the same as that of stimulation electrode section 322. Distal extension portion 324 in the form of an extension flap may be used to secure the stimulation electrode section 322 of the thin film 301. While distal extension portion 324 may not be spirally wrapped above carrier core 302, distal extension portion 324 may be wrapped (e.g., wound or folded around) over the outer surface of carrier core 302, and subsequently coated or inserted into a tube for fixation in the manner described above with regard to the first example of FIGS. 4 and 5. Depending on the width of distal extension portion 324 relative to the diameter of carrier core 302, distal extension portion 324 may extend entirely around the outer circumference of carrier core 302 or may extend around only a portion of the outer circumference of carrier core 302. Like the cable section 303, distal extension portion 324 may secure the position of stimulation electrode section 322 on carrier core 302.

Distal extension portion 324 may not include any electrodes 324. As such, distal extension portion 324 may be covered with a coating or outer tube 328, e.g., as described above with regard to the first example. The length of distal extension portion 324 may be selected to allow for sufficient "grip" of distal extension portion 324 by a coating or outer tube 328 to serve as an additional fastener. In some examples, the length of distal extension 324 may be one or a few millimeters to give sufficient surface area for grip for a shrink tube on a 1.2 mm core. In some examples, a length of approximately two or more times the core diameter may be employed to provide sufficient grip.

Figure 11:
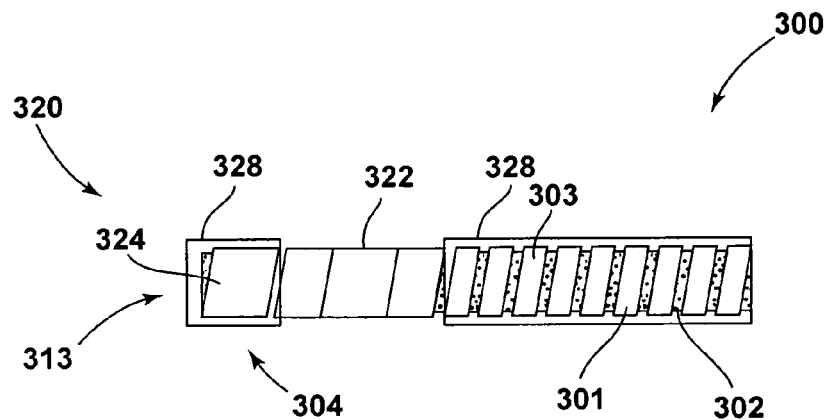
FIG. 11 is a schematic diagram illustrating a distal end of a lead according to a fifth example.
Figure 12:
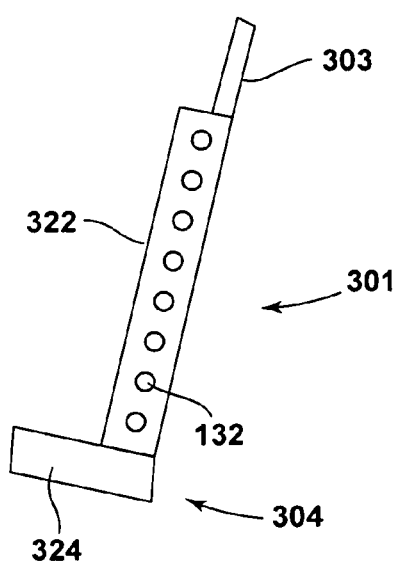
FIG. 12 is a schematic diagram illustrating the distal end of the thin film according to the example of FIG. 11.

FIG. 11 is a schematic diagram illustrating lead 300 according to a fifth example. FIG. 12 is a schematic diagram illustrating thin film 301 according to the example of FIG. 11 shown from above prior to being wrapped around carrier core 302. The fifth example may be substantially the same or similar to that of the first example shown in FIGS. 4 and 5.

However, in the fifth example, stimulation electrode section 322 may be sized and shaped to be spirally wound around carrier core 302, e.g., similar to that of cable section 303 and distal extension portion 324 spirally wrapped or coiled around carrier core 302 in the first example. As shown in FIGS. 11 and 12, stimulation electrode section 322 is a rectangular section of thin film 301 and each of cable section 303, distal extension portion 324, and stimulation electrode section 322 are wrapped around carrier core 302 to secure thin film 301 to carrier core 302. Stimulation electrode section 322 is not covered by coating and/or outer tube 328 to leave stimulation electrodes 132 in stimulation electrode section 322 uncovered to not interfere with delivery of electrical stimulation and/or sensing of electrical signals.

Figure 13:
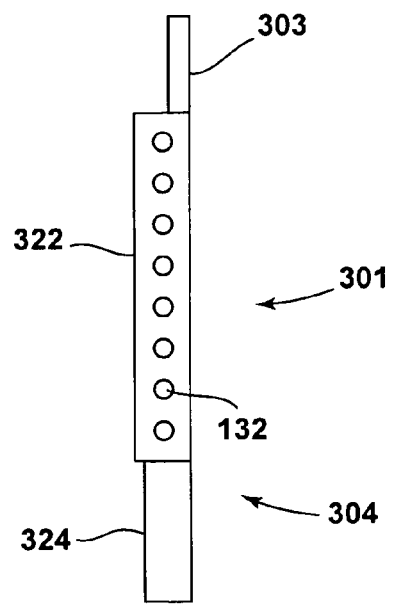
FIG. 13 is a schematic diagram illustrating an alternative of the distal end of the thin film according to the example of FIG. 11.

FIG. 13 is an alternative configuration of distal extension 324 compared to that shown in FIG. 12. In particular, in FIG. 12, distal extension 324 and stimulation electrode section 322 form an "L" configuration in which distal extension 324 extends about 90 degrees from the direction of the stimulation electrode section 322 and cable section 303. Conversely, in FIG. 13, distal extension 324 extends in a direction substantially parallel to that of stimulation electrode section 322 and cable section 303.

Figure 14:
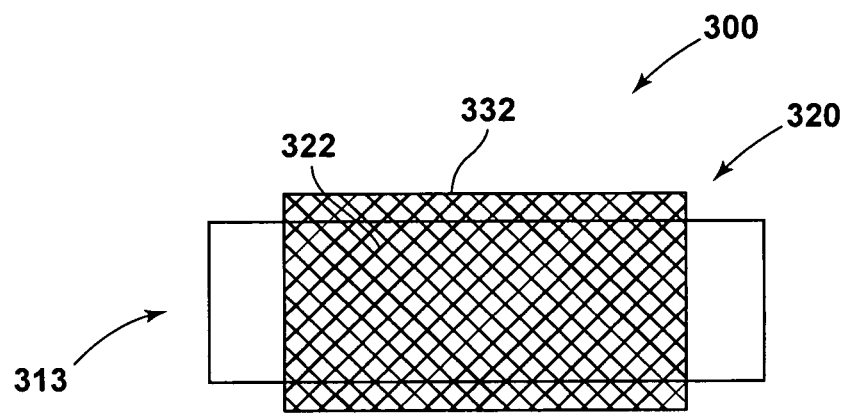
FIG. 14 is a schematic diagram illustrating a distal end of a lead according to a sixth example.
Figure 15:
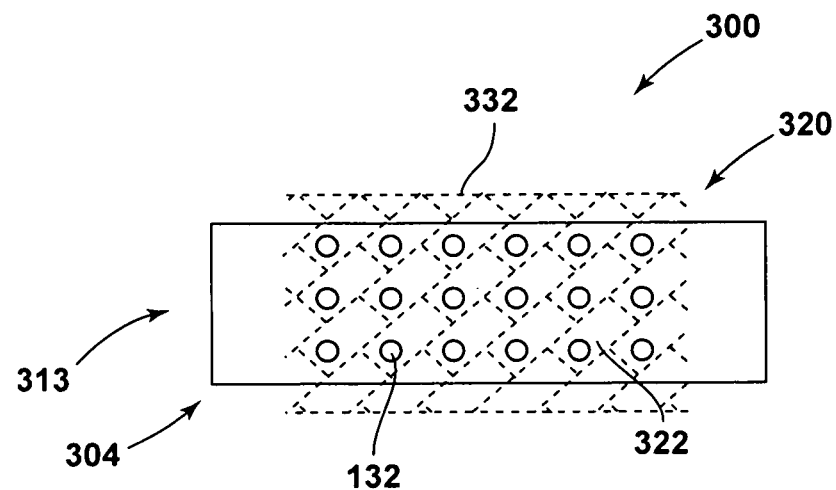
FIG. 15 is a schematic diagram illustrating a distal end of a lead according to a seventh example.

FIG. 14 is a schematic diagram illustrating stimulation electrode section 322 of lead 301 according to a sixth example. FIG. 15 is a schematic diagram illustrating stimulation electrode section 322 of lead 301 according to a seventh example. The sixth and seventh examples may be substantially the same or similar to that of the first example shown in FIGS. 4 and 5.

However, as shown, lead 300 of FIGS. 13 and 14 includes jacket tube 332 over at least a portion of stimulation electrode section 332. Jacket tube 332 is located over stimulation electrode section 322 and carrier core 302 (not shown) such that tube jacket 332 clamps stimulation electrode section 322 to carrier core 302 or otherwise secures electrode section 322 to carrier core 302. Jacket tube 332 may prevent dislocation of the stimulation electrode section 322 from carrier core 302.

In some examples, jacket tube 332 may be configured to not substantially obstruct the direct contact between the stimulation electrode 132 and surrounding brain tissue when lead 300 is inserted into the brain. To this end, the jacket tube 332 may be formed of a fine mesh, as shown in FIG. 14, and/or a tube with apertures, e.g., apertures sized and/or shaped based on the size and shape of electrodes 132, that are aligned relative to electrodes 132 on stimulation electrode section 322 of thin film 301, e.g., as shown in FIG. 15.

In the example of FIG. 14, jacket tube 332 may be a tube formed of a fine mesh material, e.g., a fine mesh formed of substantially non-electrically conductive material. For example, jacket tube 332 may have fine wires and have a relatively high aspect ratio, relatively large openings area and a relatively small filled area, e.g., to provide good accessibility of brain tissue to the electrode surface. For example, brain tissue may contact the electrodes through holes in the mesh. A majority of the electrode surfaces, e.g., approximately 80 percent or greater, may remain uncovered by fine mesh jacket tube 332. The jacket tube 332 may have a thickness of approximately 10 microns to approximately 100 microns, e.g., approx. 50 microns.

In some examples, carrier core 302 may have a diameter of between approximately 1 millimeter and approximately 2 millimeters. Surface of electrodes 132 may have a diameter of a several hundreds of microns, e.g., when electrode surface take the shape of a circular dot, and may be spaced apart from one another at a distance of about one to two hundred microns. Jacket tube 332 may be formed of a fine mesh with a mesh size that does not substantially disturb the effectiveness of electrodes 132 in delivering and/or sensing electrical signals. In some examples, the mesh size of jacket tube 332 may be selected so that holes in the jacket tube 332 are on the order of about $1/10$ of the electrode diameter and the wires of the mesh cover less than about 10 percent of the electrode surface area.

Alternatively, as shown in FIG. 15, jacket tube 332 may be a tube including a plurality of apertures that may be aligned with electrodes 132 such that jacket tube 332 does not substantially cover the outer surface of some or substantially all of electrodes 132. For example, jacket tube 332 may include apertures that are shaped, sized, and/or arranged based on the geometry and arrangement of electrodes 132 in stimulation electrode section 322. When placed over stimulation electrode section 322 on carrier core 302, the apertures may be aligned relative to electrodes 132 such that the apertures in jacket tube 332 leave the electrode surface areas substantially uncovered. In some examples, the apertures may have the same shapes as electrodes 132, while in others, the shapes may be different but the relative size of the apertures still allows for the surfaces of electrodes 132 to remain substantially uncovered by jacket tube 332.

In both cases, the mesh or apertures may, for instance, be obtained using computer controlled techniques such as laser cutting or other means. Also, jacket tube 332 may be at least partially made of a medical grade polymer, e.g. PEEK. The use of such a polymer provides the advantage that the risk of tissue reactions such as inflammation or encapsulation may be significantly decreased. Furthermore, sufficient stability may be provided. Alternatively, polyurethane or silicone for instance or other structural medical grade polymer materials or biocompatible materials may be chosen for the material for jacket tube 332.

Jacket tube 332 may be attached around the distal portion by using heat shrink tubing material. Tubing is available in a wide range of materials, e.g., polyvinylidene fluoride, non-phthalate, polyvinylchloride, polyester or the like. Before heating, the material may easily slide over the distal portion. By heating, the material may shrink and form a tight fit around the distal portion. Alternatively, swelling agents may be used to create a tight-fit arrangement. In a swollen state, the tubing may easily slide over the distal portion. Once the swelling agents are extracted, a tight fit may be obtained. Silicones tubes may be used this way.

In some examples, jacket tube 332 may be relatively thin so as not to obstruct the contact between electrodes 132 and the brain or other tissue. For example, jacket tube 332 may have a thickness of between approximately 10 microns to approximately 100 microns. Such a thickness is sufficient in terms of stability but at the same time advantageous in not obstructing the generation and transmission of the stimulation field. It is possible with such a setup to safeguard the contact between electrode and brain and provide sufficient strength for jacket tube 332.

Application of the leads and methods of the present disclosure includes the area of DBS leads. DBS leads can be manufactured with thin films, and the thin film needs to be safely secured to the core. In some instances, if only an adhesive may be used to adhesively bond the thin film to the carrier core, where the adhesive bond is the only mechanism for securing the distal portion in place, there may be possibility of delamination or detachment of portions of the thin film from the carrier core. According to examples of this disclosure, the thin film may be alternatively or additionally secured to the carrier core, e.g., by using at least one of a wind-on distal design, where a distal extension portion of the thin film is at least partially wrapped around the carrier core, or a jacket tube located around the carrier and the thin film.

While the techniques described herein are suitable for systems and methods involving DBS therapies, and may be used treat such disorders as Parkinson's disease, Alzheimer's disease, tremor, dysonia, depression, epilepsy, OCD, and other disorders, the techniques are not so limited. One or more such techniques and systems may be applied to treat disorders such as chronic pain disorders, urinary or fecal incontinence, sexual dysfunction, obesity, mood disorders, gastroparesis or diabeters, and may involve other types of stimulation such as spinal cord stimulation, cardiac stimulation, pelvic floor stimulation, sacral nerve stimulation, peripheral nerve stimulation, peripheral nerve field stimulation, gastric stimulation, or any other electrical stimulation therapy. In some cases, the electrical stimulation may be used for muscle stimulation.

In addition, it should be noted that examples of the systems and techniques described herein may not be limited to treatment or monitoring of a human patient. In alternative examples, example systems and techniques may be implemented in non-human patients, e.g., primates, canines, equines, pigs, and felines. These other animals may undergo clinical or research therapies that my benefit from the subject matter of this disclosure.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis. The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

The invention claimed is:

1. A medical device system comprising:
a thin film configured to be secured to at least a portion of a carrier core, wherein the thin film includes a distal end, a proximal end, at least one electrode between the proximal end and the distal end, and at least one electrically conductive track electrically coupled to the at least one electrode, wherein the at least one electrically conductive track extends from the at least one electrode towards the proximal end of the thin film; and
at least one fixation element configured to secure the distal end of the thin film to the carrier core, wherein the fixation element comprises at least one of a distal extension portion of the thin film configured to be at least partially wrapped around the carrier core distal to the at least one electrode or a jacket tube configured to be positioned around the carrier core and the thin film.

2. The system of claim 1, wherein the fixation element comprises the distal extension portion of the thin film.

3. The system of claim 2, wherein the thin film includes a stimulation electrode section comprising the at least one electrode, wherein the distal extension portion is distal to the stimulation electrode section of the thin film, and wherein the distal extension portion defines the distal end of the thin film.

4. The system of claim 3, further comprising at least one of a coating or outer tube covering at least a portion of the distal extension portion wound around the carrier core.

5. The system of claim 3, wherein the stimulation electrode section defines a broadened thin film section having a width greater than a width of a proximal portion of the thin film.

6. The system of claim 5, wherein the broadened thin film section is arranged asymmetrically relative to at least one adjacent section of the thin film.

7. The system of claim 3, wherein the thin film includes a cable section between the proximal end and the stimulation electrode section of the thin film, wherein the cable section includes the at least one conductive track, and wherein the stimulation electrode section is connected to the cable section of the thin film and the distal extension portion.

8. The system of claim 7, further comprising at least one of a coating or outer tube covering at least a portion of the cable section.

9. The system of claim 1, wherein the thin film includes at least one of twining extensions or a braiding extension configured to at least partially secure the thin film to the carrier core.

10. The system of claim 1, wherein the fixation element comprises the jacket tube.

11. The system of claim 10, wherein the jacket tube comprises a fine meshed jacket tube configure to be fit around the carrier core and the thin film.

12. The system of claim 10, wherein the jacket tube defines at least one aperture configured to align with the at least one electrode when the tube is positioned around the carrier core and the thin film.

13. The system of claim 10, wherein the jacket tube has a thickness of approximately 10 microns to approximately 100 microns.

14. The system of claim 1, further comprising the carrier core, wherein the thin film is wrapped at least one time around the carrier core to secure the thin film to the carrier core.

15. The system of claim 1, further comprising the carrier core, wherein the distal end of the thin film and the carrier core are bonded to each other via an adhesive, and wherein the at least one fixation element is configured to secure the distal end of the thin film to the carrier core to prevent at least one of delamination or detaching of the distal end of the thin film from the carrier core.

16. The system of claim 1, further comprising an implantable medical device, wherein the implantable medical device is configured to at least one of deliver electrical stimulation to a patient or sense electrical activity of the patient via the at least one electrode and the at least one conductive track of the thin film.

17. The system of claim 1, wherein the at least one electrode comprises a plurality of electrodes electrically isolated from each other and the at least one conductive tracks comprises a plurality conductive tracks electrically isolated from each other, and wherein each conductive track of the plurality of conductive tracks is electrically coupled to a respective electrode of the plurality of electrodes.

18. The system of claim 1, wherein the at least one electrically conductive track comprises a conductive metal.

19. A method for forming a medical device system configured for medical applications, the method comprising:
securing a thin film around at least a portion of a carrier core, wherein the thin film includes a distal end, a proximal end, at least one electrode between the proximal end and the distal end, and at least one electrically conductive track electrically coupled to the at least one electrode, wherein the at least one electrically conductive track extends from the at least one electrode towards the proximal end of the thin film; and
securing the distal end of the thin film via at least one fixation element to the carrier core, wherein the fixation element comprises at least one of a distal extension portion of the thin film at least partially wrapped around the carrier core distal to the at least one electrode or a jacket tube located around the carrier core and the thin film.

20. The method of claim 19, wherein the fixation element comprises the distal extension portion of the thin film.

21. The method of claim 20, wherein the thin film includes a stimulation electrode section comprising the at least one electrode, wherein the distal extension portion is distal to the stimulation electrode section of the thin film, and wherein the distal extension portion defines the distal end of the thin film.

22. The method of claim 21, further comprising applying at least one of a coating or outer tube over at least a portion of the distal extension portion wrapped around the carrier core.

23. The method of claim 21, wherein the stimulation electrode section defines a broadened thin film section having a width greater than a width of a proximal portion of the thin film.

24. The method of claim 21, wherein the thin film includes a cable section between the proximal end and the stimulation electrode section of the thin film, wherein the cable section includes the at least one conductive track, and wherein the stimulation electrode section is connected to the cable section of the thin film and the distal extension portion.

25. The method of claim 19, wherein the thin film includes at least one of twining extensions or braiding extensions configured to at least partially secure the thin film to the carrier core.

26. The method of claim 19, wherein the fixation element comprises the jacket tube, wherein the jacket tube comprises at least one of a fine meshed jacket tube around the carrier core and the thin film or a jacket tube including at least one aperture configured to align with the at least one electrode of the thin film when the tube is positioned around the carrier core and the thin film.

27. The method of claim 19, wherein the at least one electrode comprises a plurality of electrodes electrically isolated from each other and the at least one conductive track comprises a plurality conductive tracks electrically isolated from each other, and wherein each conductive track of the plurality of conductive tracks is electrically coupled to a respective electrode of the plurality of electrodes.

28. The method of claim 19, wherein the at least one electrically conductive track comprises a conductive metal.

29. A medical device system comprising:
an implantable medical device; and
an implantable medical lead configured to be electrically coupled to the implantable medical device, wherein the implantable medical device is configured to at least one of deliver electrical stimulation to a patient or sense electrical activity of the patient via at least one electrode of the implantable medical lead, wherein the implantable lead comprises:
a thin film configured to be secured to at least a portion of a carrier core, wherein the thin film includes a distal end, a proximal end, the at least one electrode between the proximal end and the distal end, and at least one electrically conductive track electrically coupled to the at least one electrode, wherein the at least one electrically conductive track extends from the at least one electrode towards the proximal end; and
at least one fixation element configured to secure the distal end of the thin film to the carrier core, wherein the fixation element comprises at least one of a distal extension portion of the thin film configured to be at least partially wrapped around the carrier core distal to the at least one electrode or a jacket tube configured to be positioned around the carrier core and the thin film.

30. The system of claim 29, wherein the at least one electrode comprises a plurality of electrodes electrically isolated from each other and the at least one conductive track comprises a plurality conductive tracks electrically isolated from each other, and wherein each conductive track of the plurality of conductive tracks is electrically coupled to a respective electrode of the plurality of electrodes.

31. The system of claim 29, wherein the at least one electrically conductive track comprises a conductive metal.

* * * * *